(12) United States Patent
Schultz

(10) Patent No.: US 12,194,096 B2
(45) Date of Patent: Jan. 14, 2025

(54) COMPOSITION AND METHODS FOR PREVENTING AND TREATING AFRICAN SWINE FEVER IN WILD AND DOMESTIC SWINE

(71) Applicant: Anubis Bio Corporation, San Francisco, CA (US)

(72) Inventor: Thomas A. Schultz, Oviedo, FL (US)

(73) Assignee: STEVENS LAW GROUP, San Jose, CA (US)

( * ) Notice: Subject to any disclaimer, the term of this patent is extended or adjusted under 35 U.S.C. 154(b) by 227 days.

(21) Appl. No.: 17/086,704

(22) Filed: Nov. 2, 2020

(65) Prior Publication Data

US 2021/0252148 A1    Aug. 19, 2021

Related U.S. Application Data

(60) Provisional application No. 62/928,647, filed on Oct. 31, 2019.

(51) Int. Cl.
| | | |
|---|---|---|
| *A61K 39/42* | (2006.01) | |
| *A61K 35/20* | (2006.01) | |
| *A61K 45/06* | (2006.01) | |
| *A61P 31/12* | (2006.01) | |

(52) U.S. Cl.
CPC ............ *A61K 39/42* (2013.01); *A61K 35/20* (2013.01); *A61K 45/06* (2013.01); *A61P 31/12* (2018.01)

(58) Field of Classification Search
CPC .................................................. A61K 39/42
See application file for complete search history.

(56) References Cited

U.S. PATENT DOCUMENTS

2005/0079244 A1 * 4/2005 Giffard ................ A23K 20/163
426/42
2017/0327564 A1   11/2017 Starzl

FOREIGN PATENT DOCUMENTS

CN            110078819 A      8/2019

OTHER PUBLICATIONS

Wu et al (Journal of Molecular Biology vol. 294, pp. 151-162) (Year: 1999).*
MacCallum et al (J. Mol. Biol. vol. 262, pp. 732-745) (Year: 1996).*
Skolnick et al (Trends in Biotechnology vol. 18, pp. 34-39) (Year: 2000).*
Casset (Biochemical and Biophysical Research Communications vol. 307, pp. 198-205) (Year: 2003).*
Vajdos et al (Journal of Molecular Biology vol. 320, pp. 415-428) (Year: 2002).*
Zhang et al (Chinese Veterinary Science vol. 45 (8) pp. 821-825) (Year: 2015).*
He, Y et al. Transgenic Soybean Production of Bioactive Human Epidermal Growth Factor EGF. PLoS One. Jun. 17, 2016.
Chen, X et al. Recombinant Newcastle disease virus expressing African swine fever virus protein 72 is safe and immunogenic in mice. Virologica Sinica. Apr. 2016.

* cited by examiner

*Primary Examiner* — Albert M Navarro
(74) *Attorney, Agent, or Firm* — David R. Stevens; Stevens Law Group

(57) ABSTRACT

A composition for treatment of African Swine Fever in swine includes avian-sourced antibodies specific for an African Swine Fever Virus isolate. These antibodies are produced by avian animals immunized against the African Swine Fever Virus isolate and mixed with a protective/reactive matrix obtained from, isolated from, or derived from, non-hyperimmune colostrum.

7 Claims, 3 Drawing Sheets

Suspend disclosed powdered therapeutic in water
310

Administer dissolved therapeutic orally to animal suffering from ASF
320

Observe animal for improvement in ASF symptoms
330

Fig. 3

COMPOSITION AND METHODS FOR PREVENTING AND TREATING AFRICAN SWINE FEVER IN WILD AND DOMESTIC SWINE

RELATED APPLICATION

This application claims the benefit of U.S. Provisional Application Ser. No. 62/928,647 filed Oct. 31, 2019, and entitled COMPOSITION AND METHODS FOR PREVENTING AND TREATING AFRICAN SWINE FEVER IN WILD AND DOMESTIC SWINE, which is hereby incorporated herein by reference.

FIELD OF INVENTION

The invention provides compositions and methods for prevention and treatment of African Swine Fever (ASF), a virial infection in swine.

BACKGROUND OF THE DISCLOSURE

Antibodies, both natural and their synthetic analogues, are known therapeutic agents in animals. Antibodies operate by binding between the antigen combining site on the antibody and a portion of the antigen called the antigenic determinant or epitope. Antibodies are capable of high degrees of specificity enabling targeted application to specific pathogens. However, this high specificity can lead to excessively limited binding attributes, where agents or antigens that are functionally identical do not react identically with the immunoreagent or immunotherapeutic. Cross-reactivity on the other hand is the reaction between an antigen and an antibody that was generated against a similar but different antigen. Controlled cross-reactivity may constructively be used to broaden the binding range of the antibody, enabling broad spectrum protection against pathogens other than those specifically targeted.

In mammalian species, immunity to pathogens is transferred from mother to offspring via maternal antibodies located in the placenta or colostrum. The mother transfers only those antibodies that were built up by her due to natural exposure or vaccinations. However, her level of transfer of antibodies is influenced by how recently exposure to specific pathogens occurred. If the maternal colostrum contains an insufficient quantity of antibodies specific for certain pathogens, the neonate will have a deficient level of immunity for those diseases.

Colostrum has evolved naturally in mammals specifically to deliver its components to neonates to and through the gastrointestinal tract in a very concentrated low-volume form. Colostrum is known to contain antibodies such as IgA, IgG, and IgM. Other components of colostrum include lactoferrin, lysozyme, lactoperoxidase, complement, and proline-rich polypeptides (PRP). Colostrum components have been shown to protect and support the antibody activity in the gastrointestinal tract.

The antibodies and cofactors in colostrum can provide a passive immunity to the recipient. Normally antibodies and cofactors are passed to the neonate from the mother and provide the first protection against pathogens. Colostrum components help protect maternal antibodies in their journey through the bovine digestive system and support antibody activity in the intestine. Growth factors also stimulate the development and repair of the gut. Examples of intestino-trophic growth factors include insulin-like growth factors 1 and 2, glucagon-like peptide (GLP)-2, and epidermal growth factors (EGFs).

Colostrum helps to regulate the intestinal environment, rendering it hostile to foreign pathogens. As an example, it contains lactoferrin, an iron-binding protein that prevents bacteria and viruses from obtaining iron necessary for replication. Colostrum also selectively fertilizes certain probiotic species that in turn help to ward off infection. It is a natural source of two major growth factors, transforming growth factors (TGF) alpha and beta, as well as a source of insulin-like growth factors (IGF) 1 and 2. These factors promote tissue repair and development. Colostrum is also a source of hepatocyte growth factor (HGF, also known as "scatter factor"), which stimulates the growth and expansion of intestinal wall cells. Colostrum is naturally designed to serve as a protective/reactive matrix within a gastrointestinal environment.

Specific antibody production via immunization of an avian species, for example, chickens, is well documented. When immunized with an appropriate antigen, the hen responds by producing IgY antibodies which are concentrated in the egg yolk for use by the chick during the first weeks of life. These antibodies have also been shown to be effective against pathogens residing in the gastrointestinal tract of mammals when consumed orally. However, antibody therapeutic effectiveness is diminished by passage through the stomach and exposure to gastric acid and digestion enzymes.

Past attempts at employing bovine colostrum or avian antibodies individually as a therapy for human gastrointestinal infections have resulted in poor or inconsistent clinical outcomes. However, the combination of avian-produced antibodies using bovine colostrum as a protective/reactive matrix has been demonstrated to be a reliably effective therapy for diarrhea and enteric infections in humans.

Swine share many characteristics with humans. In particular, they utilize maternal passive immunity to protect neonates, are subject to infectious diarrhea and other enteric diseases, and suffer from a lack of effective treatment for certain diarrhea infections.

African Swine Fever (ASF) is a viral disease which affects wild and domestic swine. Virulent strains result in peracute or acute hemorrahagic fever, are highly contagious, and often have a high mortality rate approaching 100%. There are multiple isolates, each with its own virulence, varying from 10 to 100%. Symptoms of ASF include high fever, decreased appetite and weakness, hemorrhage, edema, ascites, shock, diarrhea, vomiting, coughing, and difficulty breathing.

Genetic complexity of ASF isolates has made developing a vaccine difficult. Barasona et al. ((2019) First Oral Vaccination of Eurasian Wild Boar Against African Swine Fever Virus Genotype II. Frontiers in Veterinary Sci. 6: Article 137) report that a naturally attenuated non-hemadsorbing form of ASF genotype II, Lv17/WB/Rie1, provides protection against the virulent ASF isolate, Arm07. Interestingly, the vaccine was administered orally. Other studies use ASF isolates which were attenuated by genetic engineering. For example, U.S. Pat. No. 9,528,094 (which is incorporated herein by reference in its entirety) discloses a vaccine created from mutant virus ASFV-G ΔMGF, an attenuated version of the virulent ASF Virus-Georgia 2007 isolate. Similarly, U.S. Pat. No. 9,808,520 (which is incorporated herein by reference in its entirety) discloses a vaccine created from mutant virus ASFV-G Δ9GL/AUK, also an attenuated version of the virulent ASF Virus-Georgia 2007 isolate. Both vaccines protected swine from challenge by post-vaccination exposure to ASF Virus-Georgia 2007 isolate. However, the difficulty of creating these vaccines was to identify an attenuated version of the virulent strain that (1) does not cause significant illness in pigs, (2) results in antibody production in pigs, and also (3) protects the pigs from the parent virulent isolate. The attenuated versions may not protect against any other ASF isolates. Consequently, according to the current state of the art, a vaccine against each virulent isolate requires the development of an attenuated version of that virulent isolate that meets requirements (1)-(3). Therefore, it is likely that development of a vaccine against each ASF viral isolate, according to the current art, will require extensive development requiring time and resources.

SUMMARY OF THE INVENTION

The present invention may use bovine colostrum as a protective/reactive matrix in conjunction with specifically targeted avian-sourced antibodies and other immune factors directed at one or more isolates of the ASF virus to transport and introduce effective passive immunity to a swine subject in need thereof. In some embodiments, other protein sources, for example, bovine serum albumin or soy protein, may be used to protect the antibodies. Antibodies created to react with specific pathogenic targets comprising all or part of one or more ASF virus isolates are combined with the colostrum or other protein source. Targeted antibodies are embedded in the colostrum or other protein as to be reactive with the one or more ASF virus isolates they may encounter within the swine subject. The components within the matrix support and are activated by the interactions of the embedded specific antibodies, causing a cascade of immune system functions within the limited physical domain that the antibody/colostrum combination occupies (for example, the gastrointestinal tract).

In some embodiments, probiotics are included. In some embodiments, electrolytes are included. In some embodiments, intestinotrophic growth factors are included.

The present invention includes one or more of the following distinguishing attributes: (a) it enables customized design of the matrix, specific factors, and the activating events for ASF; (b) it enables dose controlled formulation of a variety of mixtures of components, which may be tuned or adjusted for effect; (c) it enables dose controlled formulation that provides specified components in excess of normal physiological gastrointestinal levels that can be achieved in natural systems; (d) it uses complex component interactions to create a systems effect that emulates a native immune system response; (e) it enables creation of a preconditioned or potentiated immune response that can be administered in its potentiated state, and subsequently activated by the presence of the target ASF virus or disease state; (f) it enables the creation of formulations that have a defined specificity or broad-spectrum effect on one or more ASF isolates, to match the needs of the specific ASF disease state, and (g) it enables the creation of formulations that can be targeted for prophylaxis as well as for treatment of ASF caused by one or a plurality of ASF virus isolates.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings.

FIG. 3 is a flow chart describing a method of treating a subject using the disclosed composition.

DETAILED DESCRIPTION OF THE INVENTION

Figure 1:
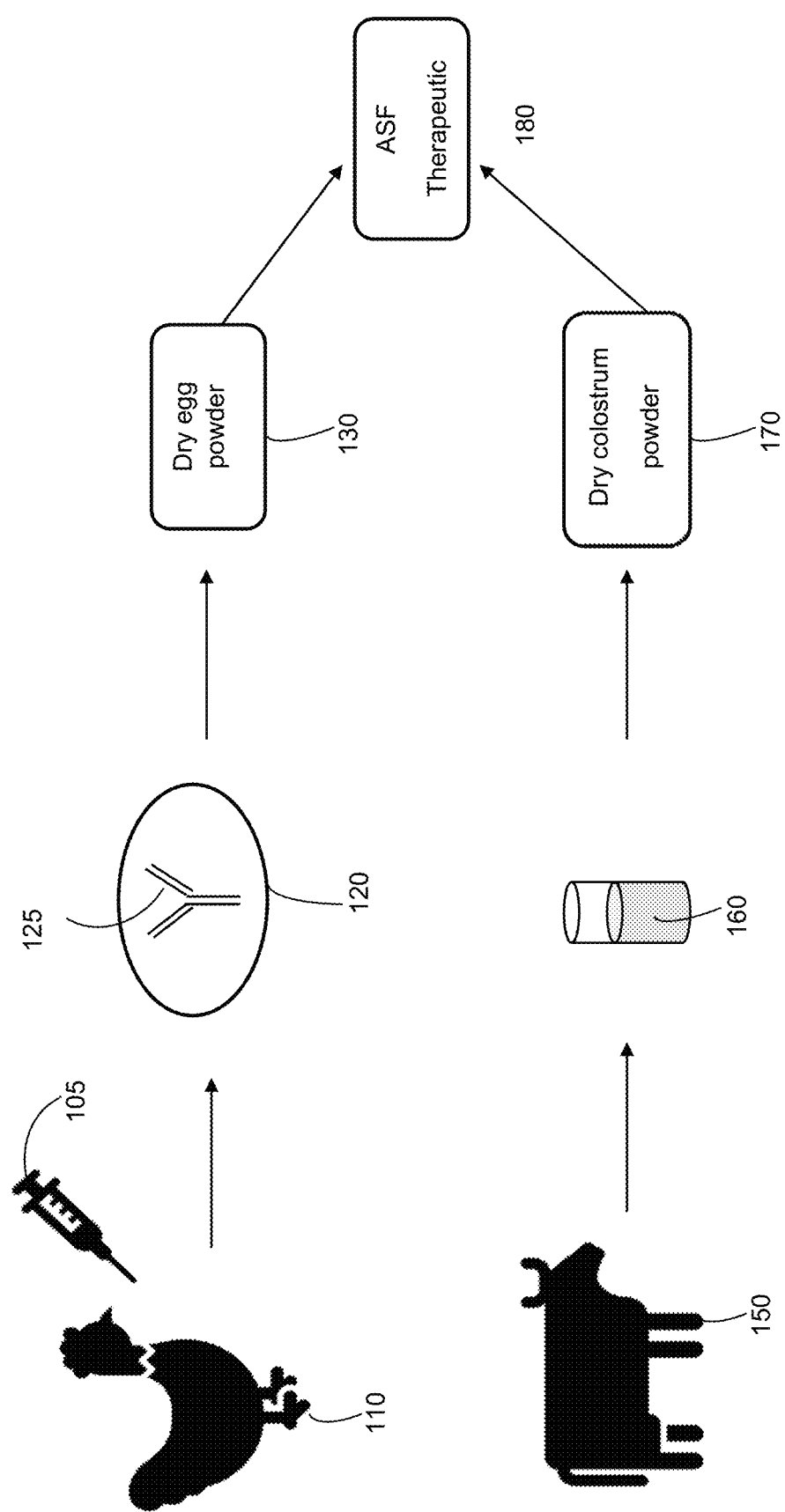
FIG. 1 is a schematic drawing of a method of producing the disclosed composition.
Figure 2:
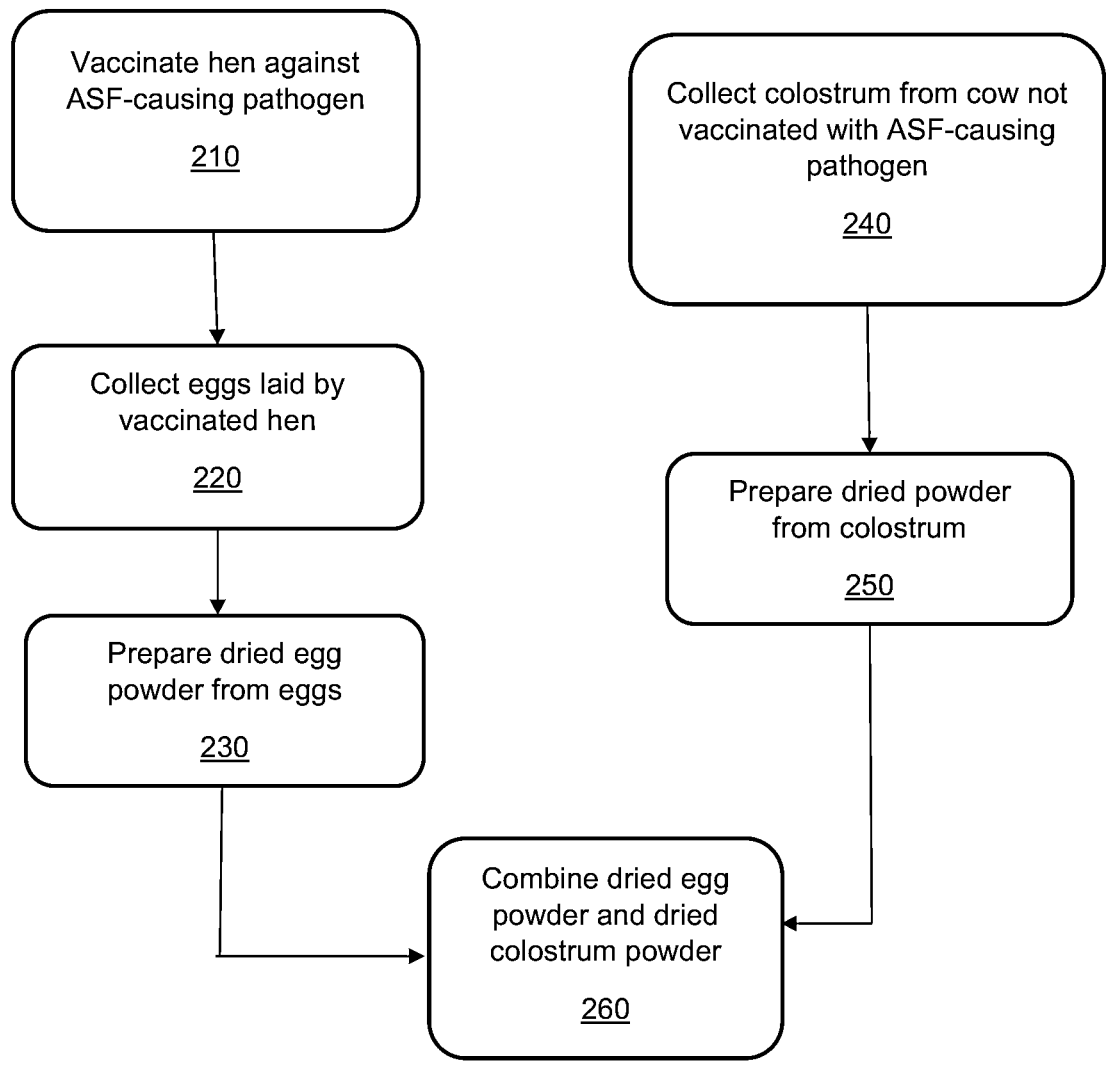
FIG. 2 is a flow chart describing a method of producing the disclosed composition.

One embodiment of the present invention is based on a method to create a targeted antibody-based formulation embedded or subsumed within a protective/reactive colostrum matrix, where the antibodies may use a controlled form of cross-reactivity to multiple clusters of related ASF viral antigens, and where the colostrum matrix may contain support and cofactors that enhance the effect of the antibodies. The utility of such antibody/matrix formulations may include providing broad-spectrum therapeutic interventions under conditions where it is known that the causative virus is an ASF virus, but the precise isolate of ASF virus is not known or under circumstances where multiple (mixed) ASF virus isolates are active.

A novel approach to the use of antibodies in this manner has been developed, that takes advantage of both the specificity and cross-reactive attributes of antibodies, and then further utilizes the components within the protective/reactive matrix to generate a multi-component in situ immune response. In this embodiment, antibodies are designed to bind to several closely related epitopes that represent a structurally related cluster of antigens found within one or more ASF virus isolates. These antigens may differ markedly in other respects and may originate from different ASF virus isolates.

One embodiment of the invention involves the method of using immune factors, (for example antibodies), within the protective/reactive matrix, where the immune factors have specificity to ASF virus antigens and are cross-reactive to antigens found in different isolates of ASF viruses. There exists a degree of structural similarity in related clusters of target antigens, without regard to the ASF isolate that is the source of the antigen. Similarity in structure can result in a phenomenon known as "cross-reactivity" (the steric binding of a reactive molecule to an antigen other than the antigen intended). Cross-reactivity is often unintentional and is considered a source of error and non-specificity. However, in this embodiment the extent and degree of cross-reactivity is controlled by various means to limit and channel its expression so as to provide desired characteristics.

In other embodiments, immune factors (for example, antibodies) directed to antigens which are specific to one or more isolates of ASF viruses may be included in the therapeutic along with the protective/reactive matrix.

This treatment confers passive immunity to subjects. The nature of the treatment makes the associated risk factors comparable to that of eating food from the source where the antibodies were harvested (e.g., risk factors would be similar to that of eating an egg and a glass of milk). This is an effective treatment with less toxicity than the currently available alternative medicines.

One embodiment of this invention is its use in the production of a broad spectrum therapeutic against a range of ASF virus isolates. One method for producing this type of reactive formulation involves the production of polyclonal antibodies harvested from an appropriately immunized animal or bird, and where such antibodies are then embedded in a protective/reactive matrix. Polyclonal antibodies (or antisera) may be antibodies that are derived from different B cell lines. Alternatively, they may be harvested from the serum, colostrum, or eggs of an immunized animal or bird.

The polyclonal antibodies disclosed herein are a mixture of immunoglobulin molecules secreted against a specific antigen, or group of antigens, recognizing a range of different epitopes present within one or more ASF virus isolates. It is possible to have multiple antibodies for a single antigen (binding to different active sites) or for a single antibody to bind to multiple antigens. This contrasts with monoclonal antibodies, which are identical and monospecific; being produced by one type of immune cell that are all clones of a single parent cell.

The antibodies used in this invention may be collected from serum, plasma, colostrum, milk, eggs, or other suitable biologically derived fluid, or from cell culture media, supernatant, etc.

The antibodies used in this invention may be treated in any suitable manner to prepare for formulation and use, including but not limited to separations, plasmapheresis, spray dry or other drying processes, lyophilization, pasteurization, and preservation methods. The antibodies used in this invention may be treated, concentrated, separated, or purified in various ways depending upon their final intended use.

Antibodies used in this invention embedded within a protective/reactive matrix may be administered in any method suitable to their immunogenic or biologically or immunologically reactive characteristics, including oral, intravenous, buccal, nasal, dermal or other method, within an appropriate protective/reactive matrix. One embodiment involves the oral administration of the antibodies so produced mixed with nonimmune colostrum as a protein source.

Many antibody agents are known to be immunogenic when administered systemically, and much of the development work in the field of therapeutic antibodies has been directed toward the development of non- or low-immunogenic versions or analogues of these molecules and factors. It has also been demonstrated that antibodies, immunoglobulins, and other biological immune factors, including those derived from non-human sources, are largely non-immunogenic when ingested by humans and other animals, presumably due to the protective nature of the gastrointestinal system.

In one embodiment, antibodies are harvested from eggs of an inoculated avian then purified or treated and combined with a protective/reactive matrix, for example, colostrum, which provides a delivery medium for oral administration of the antibody formulation. This approach may provide an effective way of reliably scaling antibody production for formulation in this manner to control titer, consistency, and continuous availability for commercial use.

In one embodiment antibodies are harvested from the eggs of an inoculated avian and may be purified or treated or retained in the egg material and added to bovine colostrum. The avian host is attractive because the ASF virus specifically infects swine. The virus does not infect humans which is the reason ASF outbreaks are a threat to a food source but not a food safety issue. An avian inoculated with a virulent strain of ASF virus is unlikely to shed virus or become ill. Consequently, antibodies against the live, virulent isolates which have no attenuation may be used to raise antibodies according to this technique. This eliminates the need to identify an attenuated form of each clinically relevant ASF virus isolate. While a virulent ASF virus isolate could not be used to vaccinate a pig because the pig would shed the virulent strain, the antibodies raised against the virulent ASF virus isolate may be provided to a swine without fear of the swine infecting other animals with the ASF virus.

In some embodiments, the inoculant or immunogen may be selected to a common or preserved component or region of the one or more ASF virus isolates, while ignoring the variable or distinguishing components or regions of the individual members of ASF virus isolates. The method involves the preparation of an appropriate immunogen with characteristics that elicit the production of antibodies that are cross-reactive to desired instances of that epitope, but which are not reactive to other epitopes, and the inoculation or exposure of the producing cells or organism to that immunogen so as to cause the production of antibodies, with the resultant antibodies being embedded within a suitable protective/reactive matrix for administration.

In other embodiments, the live parent isolate (without attenuation), an attenuated version of the live parent isolate, or an expression library created from either the parent or attenuated isolate. An example of an expression library used to raise antibodies against an ASF virus isolate is described by Lacasta et al. (2014) Expression Library Immunization Can Confer Protection against Lethal Challenge with African Swine Fever Virus. J. Virol. 88(22): 13322-32, which is hereby incorporated by reference in its entirety.

Formulations that target ASF virus isolates may be developed that use admixtures of antibodies produced according to this method to provide broad coverage of ASF disease caused by more than one ASF virus isolate. For example, in the case where two or more clusters of unrelated antigens are associated with one or more ASF virus isolate, and it is desirable to create a single formulation to address the ASF disease, an admixture of multiple antibodies or other immune factors may be prepared using this method that simultaneously provides more than one broad domain of reactivity.

There is a clear need for low cost and effective treatments for ASF in both wild and domestic pigs and orally administered antibodies are candidates for this role. In addition to demonstrated efficacy, orally administered antibodies are typically non-immunogenic. They are considered typically well tolerated with no adverse side effects reported and comparatively no different reactions than a comparable ingested food product. Notably several products containing orally administered antibody have received GRAS (Generally Recognized as Safe) certification by the FDA.

In some embodiments, the methods and compositions of the invention include one or more probiotic cultures. Probiotics are microbes that are normally found in the gut. They may be bacteria or yeast. When present in proper amounts, probiotic microbes aid in digestion, inhibit growth of pathogenic organisms, and synthesize nutrients. They may also support the host's immune system or have anti-inflammatory activity. In fact, different probiotic strains provide different benefits to the host. It is for at least this reason that probiotic supplements are often provided as a mixture of multiple strains. The mixture may include a plurality of bacteria strains, a plurality of yeast strands, or a plurality of both bacteria and yeast strains. In their absence or in reduced amounts, pathogenic microbes may proliferate in the gut creating an opportunistic infection. Severe diarrhea, often associated with ASF, is one instance in which the normal gut probiotic microbes are reduced creating an environment for pathogenic organisms to multiply.

Probiotic supplements administered orally have shown inconsistent efficacy in treating gastrointestinal disease in animals. Part of the reason is thought to be that, like the antibodies discussed herein, the probiotic microbes do not survive the acid environment of the upper gastrointestinal tract. Consequently, the protection the colostrum matrix provides to the antibodies in the disclosed therapy may also protect the probiotic microbes. Therefore, a reduced number of colony forming units (CFUs) in each dose of the disclosed therapy may provide the desired efficacy relative to providing probiotic cultures alone. Furthermore, the probiotics may add to the therapeutic effect of the antibodies in the disclosed therapy.

In some embodiments, the microbial strains which may be included as probiotics include one or more of the following list: *Enterococcus faecium* (including, but not limited to strain SF68), *Lactobacillus acidophilus*, *Lactobacillus casei*, *Lactobacillus plantarum*, *Bifidobacterium bifidum*, VSL #3, *Lactobacillus rhamnosus* (including, but not limited to strain GG (LGG)), *Bifidobacterium animalis* (including, but not limited to, strain AHC7). Other strains known in the art may also be included in the disclosed therapy.

In addition to probiotics, some embodiments may include prebiotics which provide nutrients for the probiotic microbes. The colostrum matrix may act as a prebiotic. Other prebiotics which may be included are fructooligosaccharides (FOS), beet pulp, raw garlic, dandelion greens, wheat dextrin, chicory, fermented vegetables, and other prebiotics known in the art.

One embodiment of this invention is a broad spectrum therapeutic or prophylactic antiviral formulation composed of an admixture of broad-spectrum neutralizing antibodies directed to one or more ASF virus isolates, embedded within a protective/reactive matrix, produced according to this method, for the purposes of allowing for effective administration to treat or prevent ASF disease caused by a range of ASF isolates.

One embodiment of this invention is a broad spectrum therapeutic or prophylactic antiviral formulation for administration to wild or domestic swine, embedded within a protective/reactive matrix, containing an admixture of broad-spectrum antiviral antibodies directed to one or more ASF virus isolates produced according to this method.

One important limitation of using natural food-based products is that preparations are limited to the results allowed by natural processes. The present invention allows for the selective addition of specific antibodies and general immune factors (formulations) that are significantly higher than physiological levels than can normally be achieved in nature. The present invention also allows for a weighting of various factors in a manner as to create greater specificity to targeted ASF isolates.

One embodiment of this invention uses oral administration. It has been demonstrated in both human and animal systems that oral (ingested) administration of antibodies, immunoglobulins, and other biological immune factors can have measurable effects on the course, severity and duration on diseases of, in, associated with, or influenced by, the gastrointestinal system. This effect is naturally demonstrated through the colostrum/milk mediated "acquired immunity" effect observed in most mammals. This concept has been extended through the practice of "hyper-immunized" animals. Studies have shown specific protective and therapeutic benefits from hyper-immunized colostrum.

The admixture of broad-spectrum antibodies is embedded in a within a protective/reactive matrix, such as for example colostrum for oral administration. Colostrum serves to provide additional protective and efficacious attributes to the antibody formulation. Any combination of antibodies can be used in within a colostrum matrix, including but not limited to a combination of antiviral antibodies.

Diarrhea, which often accompanies ASF infection, causes dehydration and loss of electrolytes which can be severe. Some embodiments may include one or more electrolytes. The one or more electrolyte may provide supportive therapy to recover from the dehydration and electrolyte loss caused by diarrhea. In some embodiments, the electrolyte mixture may include one or more of the following list: sodium, potassium, chloride, calcium, magnesium, and phosphate.

Several growth factors are known to be intestinotrophic. For example, glucagon-like peptide 2 (GLP-e) is a known treatment for short bowel syndrome. Others include the insulin-like growth factors and hepatocyte growth factor. Some intestinotrophic growth factors may be naturally present in the added colostrum. In some embodiments, one or more intestinotrophic growth factors may be added to the disclosed composition. In some embodiments, the added growth factors are synthesized using recombinant DNA technology. The colostrum may protect the one or more intestinotrophic growth factor from destruction in the upper gastrointestinal tract as it protects the antibodies.

The disclosed composition includes IgY antibodies may be derived from eggs laid by chickens or other avian species (egg-laying hens). These hens have been immunized against one or more pathogens which cause ASF in swine or other animals. In the example in which chickens are used to produce the eggs, the chickens may be any domestic bird of the subspecies *Gallus domesticus*. Examples include, but are not limited to, the following breeds of *Gallus domesticus*: Rhode Island Red, Leghorn, Australorp, Lohmann Brown Classic, Sussex, Golden Comet, Marans, Plymouth Rock, Barnevelder, Buff Orpington, Ameraucana, La Brese, and Hamburg. These examples are breeds of chickens which are known to be prolific egg producers. However, other breeds of chicken and other avian species are within the scope of this disclosure. In some embodiments, the chickens may comprise breeds meeting safety and process regulations for animal consumption as promulgated by relevant government authority (for example, the United States Department of Agriculture ("USDA")).

Prior to egg collection, the hens may be immunized with a vaccine comprising at least one antigen which initiates production of antibodies directed against one or more ASF-causing pathogens. The vaccine may be produced by any method known in the art. Examples include wild-type live vaccines, attenuated live vaccines, modified live vaccines, chemically altered vaccines, killed vaccines, toxoid vaccines, DNA vaccines, subunit vaccines, recombinant vaccines, polysaccharide vaccines, and conjugate vaccines. In some embodiments, the vaccines may include one or more adjuvants which enhance the immunogenicity of the vaccine.

Protocols for immunizing the hens with the vaccine may be according to those known in the art for initiating antibody production in chickens. In an example, the hens may receive two or more vaccinations at least two weeks apart. In some embodiments, the vaccinations may begin when the hens are 18 weeks of age or older. Booster vaccines may be given to the hens 6 months after the first vaccination.

In some embodiments, the vaccines are administered to the hens subcutaneously. In other embodiments, the vaccines are administered through intramuscular, oral, intravenous, buccal, nasal, or dermal procedures.

After the immunization process, whole shell eggs may be collected from the hens. The yolks of these eggs contain concentrated IgY which bind to the one or more pathogens against which the laying chicken was vaccinated. In other embodiments, the yolk of the eggs may be isolated from the egg whites.

A dehydrated egg powder may be produced from the eggs (either whole shell or isolated yolks) according to procedures known in the art. Such procedures can include but are not limited to spray drying, lyophilization, and other preservation methods used to process the eggs. In some embodiments, antibodies in the eggs may be concentrated, separated, or purified in various ways known in the art. The antibodies produced as disclosed herein may be purified, treated, or retained in the egg material for use in manufacturing the disclosed therapeutic.

The egg powder preparation may be embedded in a within a protective protein matrix, for example colostrum, for oral administration. In some embodiments, the colostrum may be bovine colostrum. In some embodiments, the colostrum may be collected from non-hyperimmune ruminants. In some embodiments, non-hyperimmune ruminants may be non-hyperimmune cattle. In some embodiments, the colostrum may comprise of whole colostrum. The colostrum may be dehydrated and ground to a powder using techniques known in the art. Methods described herein for dehydrating the egg preparation may also be used to prepare colostrum powder.

Colostrum serves to provide additional protective and efficacious attributes to the antibody preparation. Any combination of antibodies may be used within a colostrum matrix, including but not limited to a combination of anti-pathogen, anti-toxin, and anti-adhesin antibodies.

In addition to colostrum, other protein sources may be used as a protective matrix and mixed with the egg powder preparation. While colostrum includes antibodies derived from the lactating animal, its purpose in this composition is to act as a carrier and to protect the IgY antibodies derived from the egg powder preparation. Examples of other protein sources for use in preparing the protective protein matrix include serum albumin, for example, bovine serum albumin. Dehydrated egg whites may also be used as a protein matrix. While liquid egg whites as found in a chicken egg have approximately 10% protein, a more concentrated protein mixture may be created by dehydrating the egg whites to produce a powder that is added to the egg powder preparation. Protein powder derived from other animal tissues, for example, muscle, gelatin, or collagen of non-hyperimmune animals may also be dehydrated and used to create a powdered protein matrix. Yeast, whey, or whole milk are additional examples of protein sources which may be dehydrated to create a powdered protein matrix.

Once the preparation of dried egg material including antibodies and the dried colostrum are prepared, the two may be mixed to create a powdered substance for using in treating animals with ASF. The protective protein powder may be provided in proportions of between 20% to 80% by weight of the egg and protein mixture. The powdered egg mixture may be provided in proportions of between 80% and 20% by weight of the egg and protein mixture. In some embodiments, the mixture contains approximately 55% protein powder and approximately 45% powdered egg preparation by weight. In some embodiments the mixture contains approximately 45% protein powder and approximately 55% powdered egg preparation by weight. In some embodiments, the mixture contains approximately 50% protein powder and approximately 50% powdered egg preparation by weight.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention. The following examples are intended to illustrate but not limit the invention.

FIGS. 1 and 2 describe embodiments of the preparation of the egg powder and protective protein powder mixture. In FIG. 1, chicken 110 is receiving vaccine 105 which includes one or more antigens associated with ASF-causing pathogens. Chicken 110 then lays egg 120 which includes antibodies, including antibody 125 inside it. Many antibodies are present in egg 120 although only antibody 125 is depicted for purposes of clarity. Egg 120 is converted to a dry egg powder using techniques described herein. In this embodiment, the protective protein matrix is prepared from non-hyperimmune bovine colostrum. Lactating cow 150 is a non-hyperimmune animal from which colostrum 160 is collected. Colostrum 160 is converted to a dry colostrum powder 170 using techniques described herein. Dry egg powder 130 and dry colostrum powder 170 are combined in ratios disclosed herein to produce ASF therapeutic 180.

FIG. 2 is a flow chart which describes the process depicted in FIG. 1. In step 210, the hens, are vaccinated against one or more ASF-causing pathogens. After a sufficient time to raise antibodies in response to the vaccine, the hens lay eggs which are collected in step 220. The eggs contain antibodies against the epitopes in the vaccine. In step 230, dried egg powder is prepared from the eggs. In this embodiment, colostrum is used as the protective protein matrix. In step 240, colostrum from a non-hyperimmune cow is collected. Specifically, the cow has not been vaccinated against ASF-causing pathogens. The cow is milked to collect colostrum and a dried powder is prepared from the colostrum using techniques described herein (step 250). In step 260, dried egg powder from step 230 is combined with dried colostrum powder from step 250 in ratios disclosed herein to produce the therapeutic composition.

The egg and colostrum (or other matrix protein) mixture may be provided in powdered form. Alternatively, the egg and colostrum mixture may be processed to produce tablets, chewable pills, syrups, elixirs, or aqueous suspensions. Any form known in the art which may be administered orally to an animal is within the scope of this disclosure. Other additives, including preservatives or flavorings, may be included in the final mixture.

One or more of electrolytes, vitamins, and one or more probiotic cultures may also be included in the therapeutic to further support treatment of ASF. Probiotics are microbes that are normally found in the gut. They may be bacteria or yeast. When present in proper amounts, probiotic microbes aid in digestion, inhibit growth of pathogenic organisms, and synthesize nutrients. They may also support the host's immune system or have anti-inflammatory activity. In fact, different probiotic strains provide different benefits to the host. It is for at least this reason that probiotic supplements are often provided as a mixture of multiple strains. The mixture may include a plurality of bacteria strains, a plurality of yeast strains, or a plurality of both bacteria and yeast strains. In their absence or in reduced amounts, pathogenic microbes may proliferate in the gut creating an opportunistic infection. Severe diarrhea, often accompanying ASF infection, is one instance in which the normal gut probiotic microbes are reduced creating an environment for pathogenic organisms to multiply.

Probiotic supplements administered orally have shown inconsistent efficacy in treating gastrointestinal disease. Part of the reason is thought to be that, like the antibodies discussed herein, the probiotic microbes do not survive the acid environment of the upper gastrointestinal tract. Consequently, the protection the colostrum or other protein matrix provides to the antibodies in the disclosed therapy may also protect the probiotic microbes. Therefore, a reduced number of colony forming units (CFUs) in each dose of the disclosed therapy may provide the desired efficacy relative to providing probiotic cultures alone. Furthermore, the probiotics may add to the therapeutic effect of the antibodies in the disclosed therapy.

In some embodiments, the microbial strains which may be included as probiotics include one or more of the following list: *Enterococcus faecium* (including, but not limited to strain SF68), *Lactobacillus acidophilus*, *Lactobacillus casei*, *Lactobacillus plantarum*, *Bifidobacterium bifidum*, VSL #3, *Lactobacillus rhamnosus* (including, but not limited to strain GG (LGG)), *Bifidobacterium animalis* (including, but not limited to, strain AHC7). The latter is reported to be especially effective to combat *Clostridium difficile* infections of the gut. Other strains known in the art may also be included in the disclosed therapy.

In addition to probiotics, some embodiments may include prebiotics which provide nutrients for the probiotic microbes. The protein matrix may act as a prebiotic. Other prebiotics which may be included are fructooligosaccharides (FOS), beet pulp, raw garlic, dandelion greens, wheat dextrin, chicory, fermented vegetables, and other prebiotics known in the art.

The therapeutic may be provided to swine or other animals in need in doses that may depend on the animal's body weight, the severity of the disease, and whether the therapeutic is being used prophylactically or to treat existing illness. In an example, a single dose may comprise 3-10 grams of the powdered egg and protein matrix mixture, excluding other additives which may be present in the final product. In some embodiments, a single dose may comprise approximately 5 grams of the powdered egg and protein matrix mixture, excluding other additives which may be present in the final product. The therapeutic may be administered by sprinkling the dry product onto food which the animal may then ingest. The therapeutic in dry form may be mixed with water or other ingestible liquid and mixed into or decanted onto food which the animal may then ingest. The therapeutic in dry form may be mixed with water or other ingestible liquid and administered into the animal's mouth using a syringe or provided for the animal to drink or administered directly into the animal's stomach through a nasogastric tube. In summary, any method of administering the product into the gastrointestinal tract of the animal to be treated is within the scope of this disclosure.

FIG. 3 summarizes an embodiment in which an animal suffering from ASF is treated with the disclosed composition. In step 310, a user suspends the powdered therapeutic as described herein in water. The suspended therapeutic is administered orally to an animal suffering from ASF (step 320). The animal is then observed for improvement in symptoms of ASF (step 330).

The following Examples demonstrate proof of concept for the technique disclosed herein in preparing therapeutics and prophylactics against diseases in animals.

Example 1

Ingested Antibody Treatment for Diarrhea

Diarrhea is a symptom of a broad range of causes including bacterial, viral, and parasitic diseases that attack dogs and cats. Bacterial diarrhea is induced by multiple organisms, including various forms of *Escherichia coli, Salmonella, Shigella, Campylobacter* and others. Viral canine diarrhea is often caused by rotavirus, coronavirus or parvovirus, but also may be caused by several other viruses.

An example of this approach is based on known multiple causative organisms in diarrhea. These causative organisms can be organized into common clusters of structurally related toxins, to which a series of broad-spectrum neutralizing antibodies can be created that, when admixed into a formulation with clinically effective titers, can be used as a broad-spectrum organism-independent therapeutic intervention for toxin-mediated diarrhea.

Antibodies specifically bind to causative organisms of diarrhea are obtained and prepared in a powder form. An activating enzyme/protein mixture (for example, colostrum) is also prepared in a powder form. The two powders are mixed thoroughly and distributed in dried form for an oral formulation. Before administration, the powdered oral formulation is mixed with a small quantity of water prior to consumption.

This treatment confers passive immunity to patients. The nature of the treatment makes the associated risk factors comparable to that of eating food from the source where the antibodies were harvested (e.g., risk factors would be similar to that of eating an egg and a glass of milk). This is an effective treatment with greater effect and less toxicity than the currently available alternative treatments.

Example 2

Successful Antibody Treatment for Parvovirus

A six-week-old puppy was stricken with severe diarrhea and taken to a veterinary hospital for diagnosis and treatment. The attending veterinarian diagnosed the patient with parvovirus, which was confirmed with an ELISA fecal test.

Canine parvovirus is a highly contagious viral disease that can produce a life-threatening illness. The virus attacks rapidly dividing cells in a dog's body, most severely affecting the intestinal tract. Parvovirus also attacks the white blood cells, and when young animals are infected, the virus can damage the heart muscle and cause lifelong cardiac problems.

There are no drugs or treatments generally available that can kill parvovirus. Standard of care treatment consists of aggressive supportive care to control symptoms. Dogs infected with parvovirus need intensive treatment in a veterinary hospital, where they receive antibiotics (which has no effect on the parvovirus), drugs to control the vomiting, intravenous fluids and other supportive therapies. This entails considerable expense; the average hospital stay is 5 to 7 days at a cost of several thousand dollars. Even with medical support canine parvovirus mortality rates range from 20%-50%.

With the pet owner's permission, in addition to standard-of-care treatment, the attending veterinarian administered an antibody treatment consisting of hyperimmunized egg powder containing parvovirus antibodies mixed with whole colostrum powder. The formulation was mixed with a small quantity of water and administered orally to the patient, who was taken home by the owner. The next morning the patient was reexamined at the hospital by the veterinarian. The puppy was symptom free, with normal temperature, solid stool, and no evidence of physical distress. A fecal ELISA test confirmed the absence of parvovirus infection. The antibody/colostrum formulation effectively conferred passive immunity to the patient and eradicated the parvovirus infection and sequelae within 24 hours of treatment.

I claim:

1. A composition for treatment of African Swine Fever in swine, the composition comprising
    avian-sourced polyclonal antibodies specific for an African Swine Fever Virus isolate, wherein said polyclonal antibodies are produced by avian animals immunized against the African Swine Fever Virus isolate; and
    a protective/reactive matrix obtained from, isolated from, or derived from, non-hyperimmune colostrum, wherein the composition is administered to an animal to prevent or treat an occurrence of African Swine Fever in the animal.

2. The composition of claim 1, wherein the non-hyperimmune colostrum is at least part bovine derived.

3. The composition of claim 1, further comprising at least one probiotic culture.

4. The composition of claim 1, further comprising at least one prebiotic.

5. The composition of claim 1, further comprising a mixture of electrolytes.

6. The composition of claim 1, further comprising at least one growth factor.

7. The composition of claim 1, further comprising at least one intestinotrophic growth factor.

* * * * *